US012733983B2

(12) United States Patent
Hwang et al.

(10) Patent No.: US 12,733,983 B2
(45) Date of Patent: Sep. 15, 2026

(54) THORACOSCOPY SIMULATION APPARATUS AND METHOD BASED ON THREE- DIMENSIONAL ATELECTASIS MODEL

(71) Applicant: Korea University Research and Business Foundation, Seoul (KR)

(72) Inventors: In Tae Hwang, Seoul (KR); Jin Wook Hwang, Seoul (KR); Seung Hak Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 101 days.

(21) Appl. No.: 18/841,646

(22) PCT Filed: Mar. 16, 2023

(86) PCT No.: PCT/KR2023/003498
§ 371 (c)(1),
(2) Date: Mar. 13, 2025

(87) PCT Pub. No.: WO2023/177225
PCT Pub. Date: Sep. 21, 2023

(65) Prior Publication Data

US 2025/0387163 A1 Dec. 25, 2025

(30) Foreign Application Priority Data

Mar. 16, 2022 (KR) ........................ 10-2022-0032481

(51) Int. Cl.
*A61B 34/10* (2016.01)
*G06T 7/00* (2017.01)
(Continued)

(52) U.S. Cl.
CPC ............ *A61B 34/10* (2016.02); *G06T 7/0016* (2013.01); *G06T 7/13* (2017.01); *G06T 7/66* (2017.01);
(Continued)

(58) Field of Classification Search
CPC ..... A61B 34/10; A61B 6/50; A61B 2034/105; A61B 2034/2065; A61B 2090/3762;
(Continued)

(56) References Cited

U.S. PATENT DOCUMENTS 12,004,815 B2 * 6/2024 Sartor .................. A61B 6/5247
2010/0027861 A1 * 2/2010 Shekhar ............... G06V 10/755 382/128
(Continued)

FOREIGN PATENT DOCUMENTS

KR 1020100028301 B1 12/2010
KR 101092470 B1 12/2011
(Continued)

OTHER PUBLICATIONS

Hwang, Intae, "CT Image-Based Atelectasis Simulation and Lung Nodule Localization System", The Korean Society for Thoracic & Cardiovascular Surgery, Nov. 4, 2021.
(Continued)

*Primary Examiner* — Baisakhi Roy
(74) *Attorney, Agent, or Firm* — CM Law LLP; Robert C. Klinger

(57) ABSTRACT

The present invention relates to a thoracoscopy simulation apparatus and method for performing a simulation that includes generating a 3D atelectasis model on the basis of a CT lung image and displaying the location of a pulmonary nodule and a safe resection margin. The thoracoscopy simulation method according to the present embodiment is a thoracoscopy simulation method in which at least a portion
(Continued)

Start

Change the 3D lung model to generate a 3D atelectasis model in an expiratory state Generate a 3D thorax model using the 3D atelectasis model and locations of ribs included in the chest CT image — S830

End of each step is performed by a processor, and may comprise the steps of: generating a 3D lung model in which a pulmonary nodule is displayed, the 3D lung model being generated on the basis of a chest CT image of a patient in an inspiratory state; changing the 3D lung model to generate a 3D atelectasis model in an expiratory state; generating a 3D thorax model using the 3D atelectasis model and the location of the ribs included in the chest CT image; and positioning the 3D thorax model in a virtual space and generating a simulation image on the basis of the 3D thorax model and the tracked locations of a thoracoscope and a surgical tool.

12 Claims, 7 Drawing Sheets

(51) Int. Cl.

| | |
|---|---|
| ***G06T 7/13*** | (2017.01) |
| ***G06T 7/66*** | (2017.01) |
| ***G06T 7/73*** | (2017.01) |
| ***G06T 17/00*** | (2006.01) |
| ***G06T 19/20*** | (2011.01) |
| ***G16H 50/50*** | (2018.01) |
| *A61B 1/313* | (2006.01) |
| *A61B 6/50* | (2024.01) |
| *A61B 34/20* | (2016.01) |
| *A61B 90/00* | (2016.01) |

(52) U.S. Cl.

CPC ................ *G06T 7/75* (2017.01); *G06T 17/00* (2013.01); *G06T 19/20* (2013.01); *G16H 50/50* (2018.01); *A61B 1/313* (2013.01); *A61B 6/50* (2013.01); *A61B 2034/105* (2016.02); *A61B 2034/2065* (2016.02); *A61B 2090/3762* (2016.02); *G06T 2200/24* (2013.01); *G06T 2207/10068* (2013.01); *G06T 2207/10081* (2013.01); *G06T 2207/30064* (2013.01); *G06T 2210/41* (2013.01); *G06T 2219/2004* (2013.01); *G06T 2219/2016* (2013.01)

(58) Field of Classification Search

CPC .. A61B 6/00; A61B 6/03; A61B 17/00; A61B 6/032; A61B 6/5211; A61B 2017/00809; G06T 7/0016; G06T 7/13; G06T 7/66; G06T 7/75; G06T 17/00; G06T 19/20; G06T 2200/24; G06T 2207/10068; G06T 2207/10081; G06T 2207/30064; G06T 2210/41; G06T 2219/2004; G06T 2219/2016

See application file for complete search history.

(56) References Cited

U.S. PATENT DOCUMENTS

| | | | | |
|---|---|---|---|---|
| 2018/0146839 | A1* | 5/2018 | Friedlander ........ | A61B 1/00048 |
| 2018/0161102 | A1 | 6/2018 | Wei et al. | |
| 2019/0125279 | A1* | 5/2019 | Peikert ..................... | A61B 8/13 |
| 2020/0030033 | A1* | 1/2020 | Sartor ................... | G06T 7/0016 |
| 2020/0035348 | A1* | 1/2020 | Sartor .................. | A61B 90/361 |
| 2020/0246073 | A1 | 8/2020 | Rossetto et al. | |

FOREIGN PATENT DOCUMENTS

| | | | |
|---|---|---|---|
| KR | 1020120122542 | B1 | 11/2012 |
| KR | 1020170096088 | A | 8/2017 |
| KR | 1020190096575 | B1 | 4/2020 |
| KR | 1020200089146 | A | 7/2020 |

OTHER PUBLICATIONS

International Search Report and Written Opinion received in Patent Cooperation Treaty Application No. PCT/KR2023/003498, mailed Jun. 20, 2023.

Lee, Joon-Ku, et al., “Segmentation and Visualization of Human Anatomy Using Medical Imagery”, The Journal of the Korea Institute of Electronic Communication Sciences, vol. 8, No. 1, Jan. 2013.

Office Action received in Korean Application No. 10-2022-0032481, dated Apr. 25, 2024.

Alvarez, Pablo, et al. “A Biomechanical Model of Lung Deflation During VATS for the Localization of Small Nodules,” HAL Open Science, Surgetica 2017, Nov. 2017, Strasbourg, France. hal-03582119, Feb. 21, 2022.

Alvarez, Pablo, et al. “A Hybrid, Image-Based and Biomechanics-Based Registration Approach to Markerless Intraoperative Nodule Localization During Video-Assisted Thoracoscopic Surgery,” Med Image Anal. Author Manuscript Oct. 10, 2022.

Lesage, Anne-Cecile, et al. “Preliminary Evaluation of Biomechanical Modeling of Lung Deflation During Minimally Invasive Surgery Using Pneumothorax Computed Tomography Scans,” IPEM Institute of Physics and Engineering in Medicine, IOP Publishing, Phys. Med. Biol. 65 (2020) 225010, Nov. 12, 2020.

Nia, Peyman Sardari, et al. “Interactive 3D Reconstruction of Pulmonary Anatomy for Preoperative Planning, Virtual Simulation, and Intraoperative Guiding in Video-Assisted Thoracoscopic Lung Surgery,” Innovations 2019, vol. I4(I) I7-26; The Author(s) 2019; sagepub.com/journals-permissions DOI: I0.II77/I5569845I982632I; journals.sagepubl.com/home/inv.

Written Decision on Registration in Korean Application No. 10-2022-0032481, dated Feb. 4, 2025.

* cited by examiner

Figure 2:
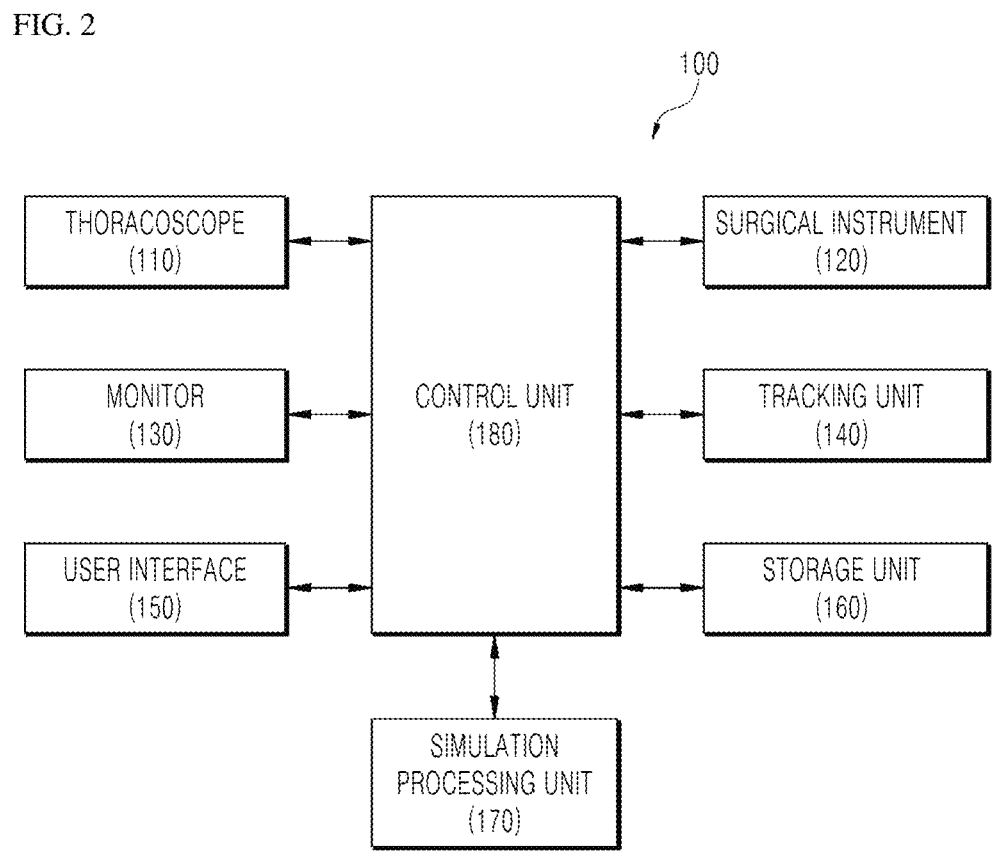

THORACOSCOPE (110)

SURGICAL INSTRUMENT (120)

MONITOR (130)

CONTROL UNIT (180)

TRACKING UNIT (140)

USER INTERFACE (150)

STORAGE UNIT (160)

SIMULATION PROCESSING UNIT (170)

PROCESSOR (191)

MEMORY (192)

THORACOSCOPY SIMULATION APPARATUS AND METHOD BASED ON THREE- DIMENSIONAL ATELECTASIS MODEL

CROSS-REFERENCE TO RELATED APPLICATION

This patent application is a National Stage entry of Patent Cooperation Treaty Application No. PCT/KR2023/003498 filed Mar. 16, 2023, which claims the benefit and priority of Korean Patent Application No. 10-2022-0032481 filed Mar. 16, 2022, the disclosures of which are incorporated by reference herein in their entirety as part of the present application.

TECHNICAL FIELD

The present disclosure relates to a thoracoscopy simulation apparatus and method for performing a simulation that includes generating a 3D atelectasis model based on a lung CT image and displaying the location of a pulmonary nodule and a safe resection margin.

BACKGROUND ART

A lung cancer is the third most common cancer in 2018, following a stomach cancer and a thyroid cancer, and the number of annual cases in Korea has been steadily increasing since 2016. Every two years, low-dose chest CT (computed tomography) tests are performed on smokers aged 54 or older, and through this, the detection rate of pulmonary nodules that may have the possibility of early stage lung cancer is increasing. Lungs, unlike other body tissues, are displayed in black on CT images, and pulmonary nodules are masses of 30 mm or less and, unlike the lungs, are displayed as white circular dots.

To segment the lungs in chest CT lung images, a lung segmentation method using distribution of intensity values of pixels/voxels is used. Using the characteristics of the lungs, which are displayed in black in CT images, boundaries are obtained using a difference in brightness (intensity) between the lungs and other body tissues, and these boundaries are overlapped to create a 3D lung model.

Chest CT scanning for medical staffs to diagnose pulmonary nodules is performed when a patient is in a maximal inspiratory state, and the result of the CT scan is an image taken when the lungs are at their largest size. However, when the medical staff performs an actual surgery to remove a pulmonary nodule, the surgery is performed in the patient's expiratory state, and the lungs become an atelectasis state (collapsed lung state) that the lungs are collapsed due to gravity depending on the patient's posture.

Atelectasis is a condition in which all or part of the lung is contracted in situations where breathing is difficult, such as blocked bronchial tubes or lung surgery. The atelectasis is caused as the lung is physically blocked due to discharges from various diseases or diseases such as a lung cancer. The lung has the largest volume during CT scan, and the volume is reduced to about 30 to 40% of the maximum volume in an atelectasis state. Therefore, it is possible to secure a space for a thoracic surgical instrument (surgical tool) to move in proportion to the reduced volume within the chest. CT imaging is performed with maximum breathing, but a surgery is performed in an atelectasis state where air has been exhausted from the lungs, so there is a big gap between the location of a pulmonary nodule visible in a CT image and the state of lungs and the location of the pulmonary nodule which can be seen in the actual surgery. This causes a difficulty in specifying the actual location of the pulmonary nodule for resection of the pulmonary nodule during surgery.

Accordingly, various auxiliary procedures are being performed to track how the location of the pulmonary nodule in an atelectasis state has changed during surgery, but there is a problem that they are not of great help in the patient's recovery and a main surgery.

Meanwhile, methods for marking (indicating) the location of a pulmonary nodule required to be surgically removed during pulmonary nodule surgery include staining, hook wiring, radiopharmaceutical injection, near-infrared fluorescent material injection, and the like. However, these additional procedures have problems in that it is difficult to identify the location of a pulmonary nodule in an actual operating room, a large amount of intact tissues must be incised, and the operator and patient are continuously exposed to radiation and fluorescent substances during surgery. Furthermore, the patient's recovery is slow and there is a risk of hemorrhage from the lungs and air embolism during procedures, so it can be said that the harm to the patient is greater than the benefit gained from the procedures.

The above-described background technology is technical information that the inventors have held for the derivation of the present disclosure or that the inventors acquired in the process of deriving the present disclosure. Thus, the above-described background technology cannot be regarded as known technology disclosed to the general public prior to the filing of the present application.

DISCLOSURE OF INVENTION

Technical Problem

One object of the present disclosure is to solve the problem of the related art that various auxiliary procedures are being performed to track how the location of a pulmonary nodule in an atelectasis state has changed during surgery but they are not of great help in the patient's recovery and a main surgery.

One object of the present disclosure is to create a 3D lung model from a lung CT image to simulate an atelectasis state and visualize the actual location of a pulmonary nodule during surgery, so that there is no need to perform additional auxiliary procedures before surgery, and the operator and patient do not have to be exposed to radiation and fluorescent substances during surgery.

One object of the present disclosure is to simulate an atelectasis state by generating a 3D lung model from a CT image of lungs in an inspiratory state.

The problems to be solved by the present disclosure are not limited to the problems mentioned above, and other problems and advantages of the present disclosure that are not mentioned can be understood through the following description and can be understood more clearly through the exemplary embodiments of the present disclosure. Also, one object of the present disclosure is to solve the problem of the related art that various auxiliary procedures are being performed to track how the location of a pulmonary nodule in an atelectasis state has changed during surgery but they are not of great help in the patient's recovery and a main surgery.

One object of the present disclosure is to create a 3D lung model from a lung CT image to simulate an atelectasis state and visualize the actual location of a pulmonary nodule during surgery, so that there is no need to perform additional auxiliary procedures before surgery, and the operator and patient do not have to be exposed to radiation and fluorescent substances during surgery.

One object of the present disclosure is to simulate an atelectasis state by generating a 3D lung model from a CT image of lungs in an inspiratory state.

The object to be achieved by the present invention is not limited to the above-mentioned object, and other object and advantages of the present invention that are not mentioned will be understood by the following description and will be more clearly understood by embodiments of the present invention. In addition, it will be appreciated that the objects and advantages that the present invention intends to solve can be realized by the means indicated in the patent claim and a combination thereof.

Solution to Problem

A thoracoscopy simulation method according to an exemplary embodiment of the present disclosure, in which at least a portion of each step is performed by a processor of a thoracoscopy simulation apparatus, may include generating a three-dimensional (3D) lung model, in which a pulmonary nodule is displayed, the 3D lung model being generated based on a chest CT image of a patient in an inspiratory state, changing the 3D lung model to generate a 3D atelectasis model in an expiratory state, generating a 3D thorax model using the 3D atelectasis model and locations of ribs included in the chest CT image, and positioning the 3D thorax model in a virtual space and generating a simulation image based on the 3D thorax model and tracked locations of a thoracoscope and a surgical instrument.

A thoracoscopy simulation apparatus according to an exemplary embodiment of the present disclosure may include a processor, and a memory that is operably connected to the processor and stores at least one code to be performed by the processor, in which when the memory is executed through the processor, the memory may store a code that causes the processor to generate a three-dimensional (3D) lung model, in which a pulmonary nodule is displayed, based on a chest CT image of a patient in an inspiratory state, generate a 3D atelectasis model in an expiratory state by changing the 3D lung model, generate a 3D thorax model using the 3D atelectasis model and locations of ribs included in the chest CT image, and position the 3D thorax model in a virtual space and generate a simulation image based on the 3D thorax model and tracked locations of a thoracoscope and a surgical instrument.

In addition to these embodiments, another method and system for implementing the present disclosure, and a computer-readable recording medium storing a computer program for executing the method may be further provided.

Other aspects and features as well as those described above will become clear from the accompanying drawings, the claims, and the detailed description of the present disclosure.

Advantageous Effects of Invention

According to the present disclosure, additional auxiliary procedures before surgery that were previously performed can be omitted, and an actual pulmonary nodule localization time during surgery can be reduced, thereby reducing operation time and the burden of additional risks for procedures.

In addition, in the existing method, the short duration of radiation and chemicals forced an operator to perform excessive resection and an operation within a limited time. However, by tracking the location of a pulmonary nodule in real time and marking (displaying) a resection margin, the operator can operate safely and effectively.

In addition, through simulation of an atelectasis state (collapsed lung state), various risk factors that may occur during actual operation can be recognized and prepared for before the operation, and surgical education on a pulmonary nodule removal surgery can be performed.

The effects of the present disclosure are not limited to those mentioned above, and other effects not mentioned can be clearly understood by those skilled in the art from the following description.

BRIEF DESCRIPTION OF DRAWINGS

FIG. 2 is a block diagram for schematically explaining the configuration of a thoracoscopy simulation apparatus according to an exemplary embodiment of the present disclosure.

FIG. 5 is an exemplary diagram illustrating a pulmonary nodule marked (displayed) on a 3D thorax model and a safe margin for removing the pulmonary nodule according to an exemplary embodiment of the present disclosure.

BEST MODE FOR CARRYING OUT THE INVENTION

The foregoing and other aspects, features, and advantages of the invention, as well as the following detailed description of the embodiments, will be better understood when read in conjunction with the accompanying drawings. However, this invention is not limited to the embodiments presented below, but can be implemented in various different forms, and should be understood to include all transformations, equivalents, or substitutes included in the spirit and technical scope of this invention. The embodiments presented below are provided to ensure that the disclosure of the present invention is complete, and to fully inform those skilled in the art of the present invention of the present invention. In describing the present invention, when it is determined that a detailed description of related known technologies may obscure the gist of the present invention, the detailed description thereof will be omitted.

The terms used in this application are used only to describe specific embodiments and are not intended to limit the present invention. Singular expressions include plural expressions unless the context clearly indicates otherwise. In this application, terms such as “including” or “have” or “comprising” are intended to designate the existence of features, numbers, steps, operations, components, parts, or combinations thereof described in the specification, and should be understood not to preclude the existence or addition of one or more other features, numbers, steps, operations, components, parts, or combinations thereof. Terms such as first, second, etc. may be used to describe various components, but components should not be limited by these terms. The terms are used only for the purpose of distinguishing one component from another.

In addition, in this application, “part” may be a hardware component such as a processor or circuit, and/or a software component executed by a hardware component such as a processor.

Hereinafter, embodiments according to the present invention will be described in detail with reference to the accompanying drawings, and in describing with reference to the accompanying drawings, the same or corresponding components will be assigned the same drawing number, and redundant descriptions thereof will be omitted.

Figure 1:
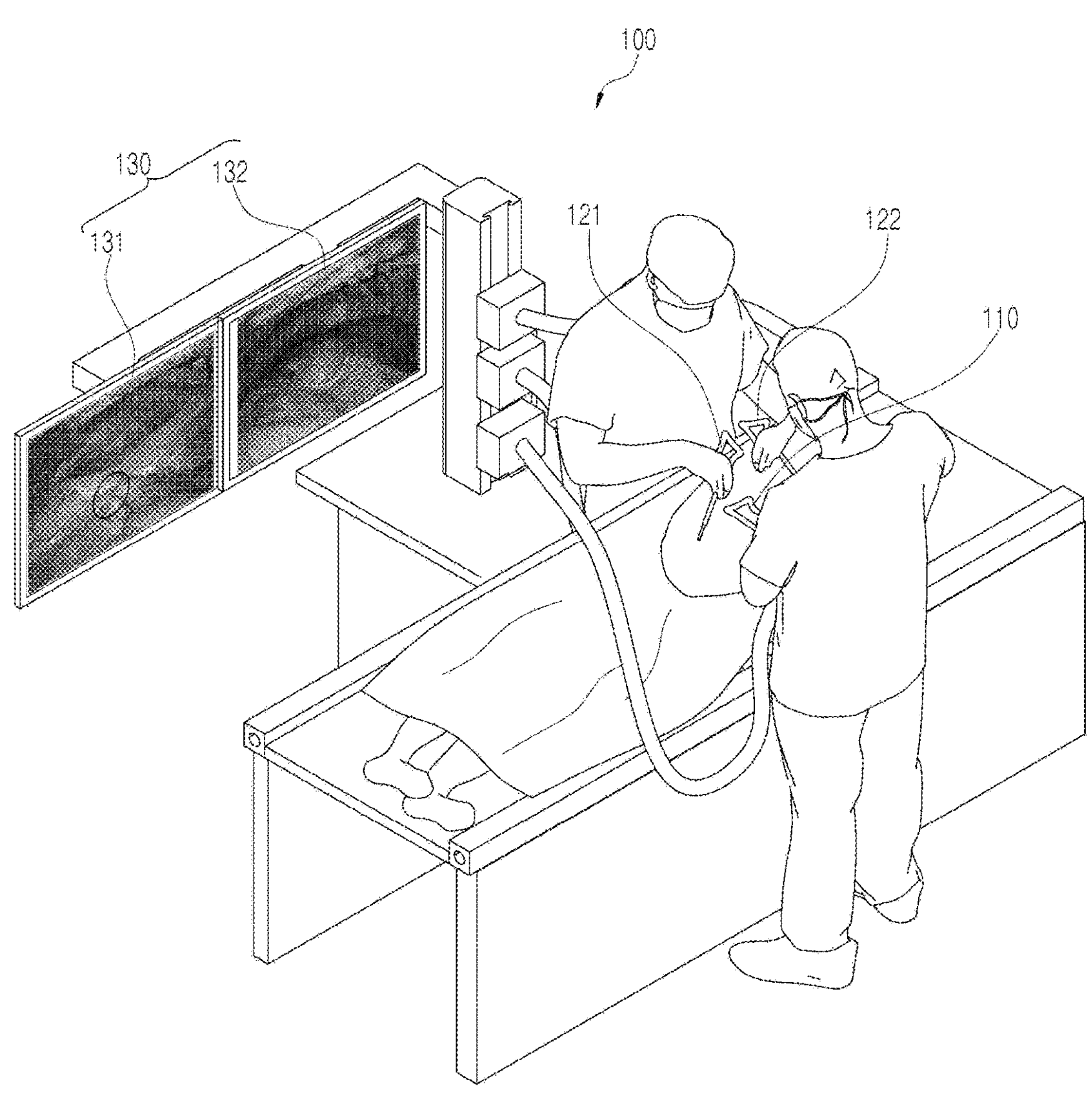
FIG. 1 is an exemplary diagram of a thoracic surgery environment based on a thoracoscopy simulation apparatus according to an exemplary embodiment of the present disclosure.

FIG. 1 is an exemplary diagram of a thoracic surgery environment based on a thoracoscopy simulation apparatus according to an exemplary embodiment of the present disclosure. Referring to FIG. 1, when performing surgery inside a patient’s chest, thoracotomy surgery has been performed by opening the patient’s chest in the past, but recently video-assisted thoracic surgery (VATS) is being performed.

Video-assisted thoracic surgery performed by the thoracoscopy simulation apparatus 100 may be a method of drilling 3 or 4 small (e.g., about 1 to 2 cm) holes in a patient’s chest, inserting a thoracoscope (110 of FIG. 2) connected to a monitor (131 of FIG. 2) through one of the holes, and inserting a surgical instrument (or surgical tool) (120 of FIG. 2) through another hole, such that an operator executes thoracic surgery by manipulating the thoracoscope (110 of FIG. 2) and the surgical instrument (120 of FIG. 2).

This video-assisted thoracic surgery may be applied widely, from surgeries such as relatively simple hyperhidrosis or simple benign diseases such as pneumothorax to highly difficult surgeries such as lung cancer resection. The range of the video-assisted thoracic surgery is increasing because it not only provides mild pain, rapid recovery after surgery, and excellent cosmetic effects, compared to thoracotomy, but also reduces hospital bills by shortening hospitalization.

In this exemplary embodiment, the thoracoscopy simulation apparatus 100 is disclosed as being applied to an actual video-assisted thoracic surgery, but is not limited to this, and may operate even in a virtual surgical environment other than an actual surgical environment when the patient’s information (surgical posture and chest CT images) is already stored.

Figure 3:
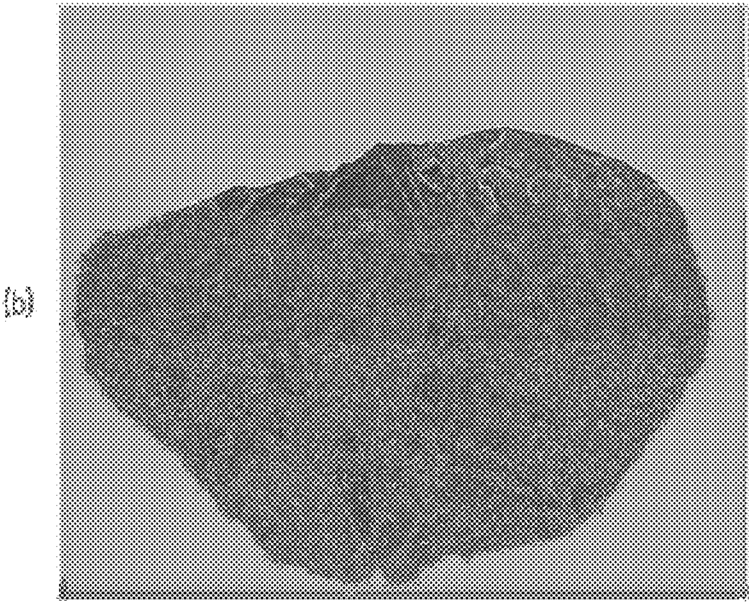
FIG. 3 is an exemplary diagram illustrating a lung model in a maximal inspiratory state and a lung model in a maximal expiratory state according to an exemplary embodiment of the present disclosure.
Figure 4:
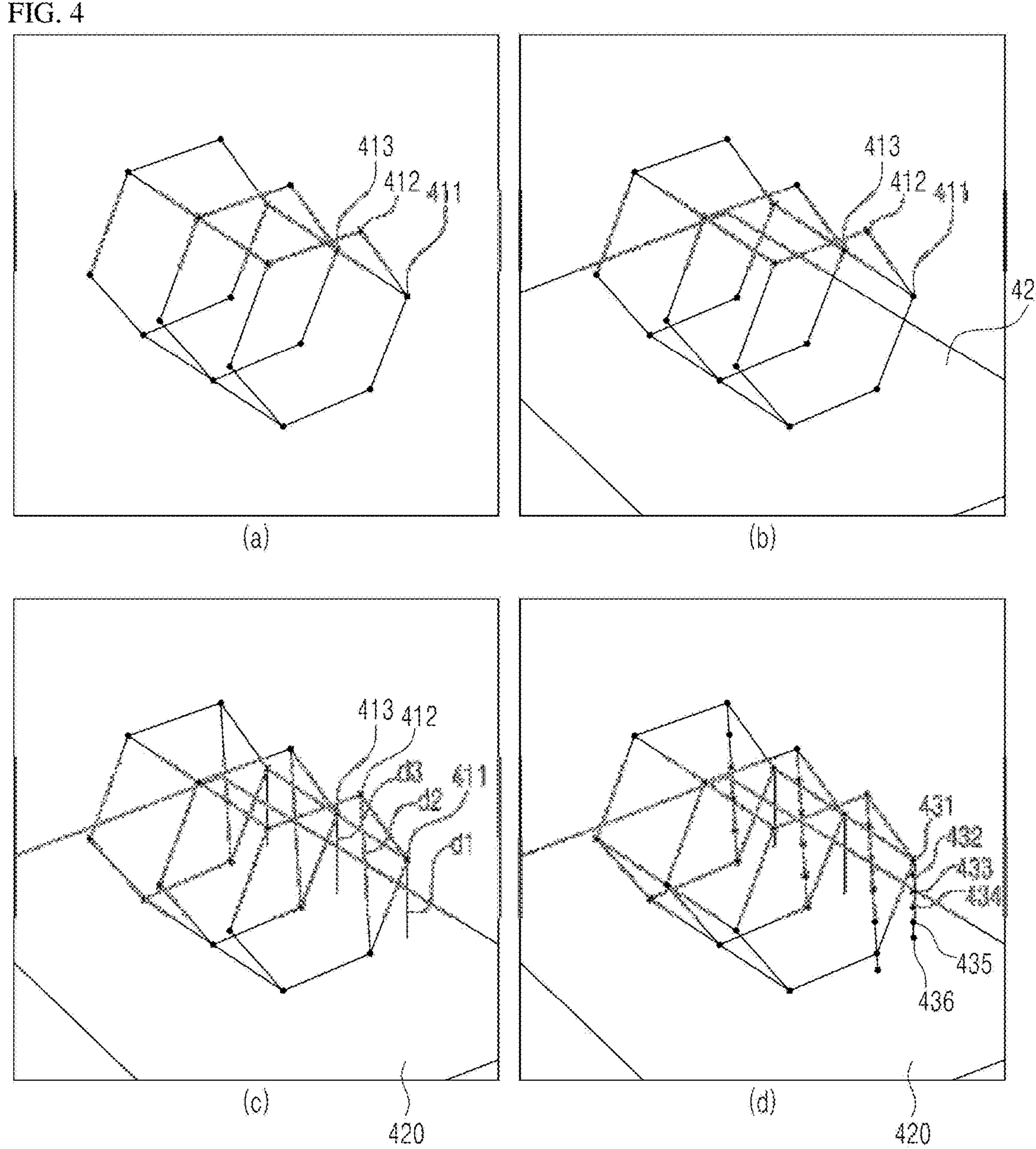
FIG. 4 is an exemplary diagram for explaining the creation of a 3D atelectasis model in an expiratory state according to an exemplary embodiment of the present disclosure.
Figure 5:
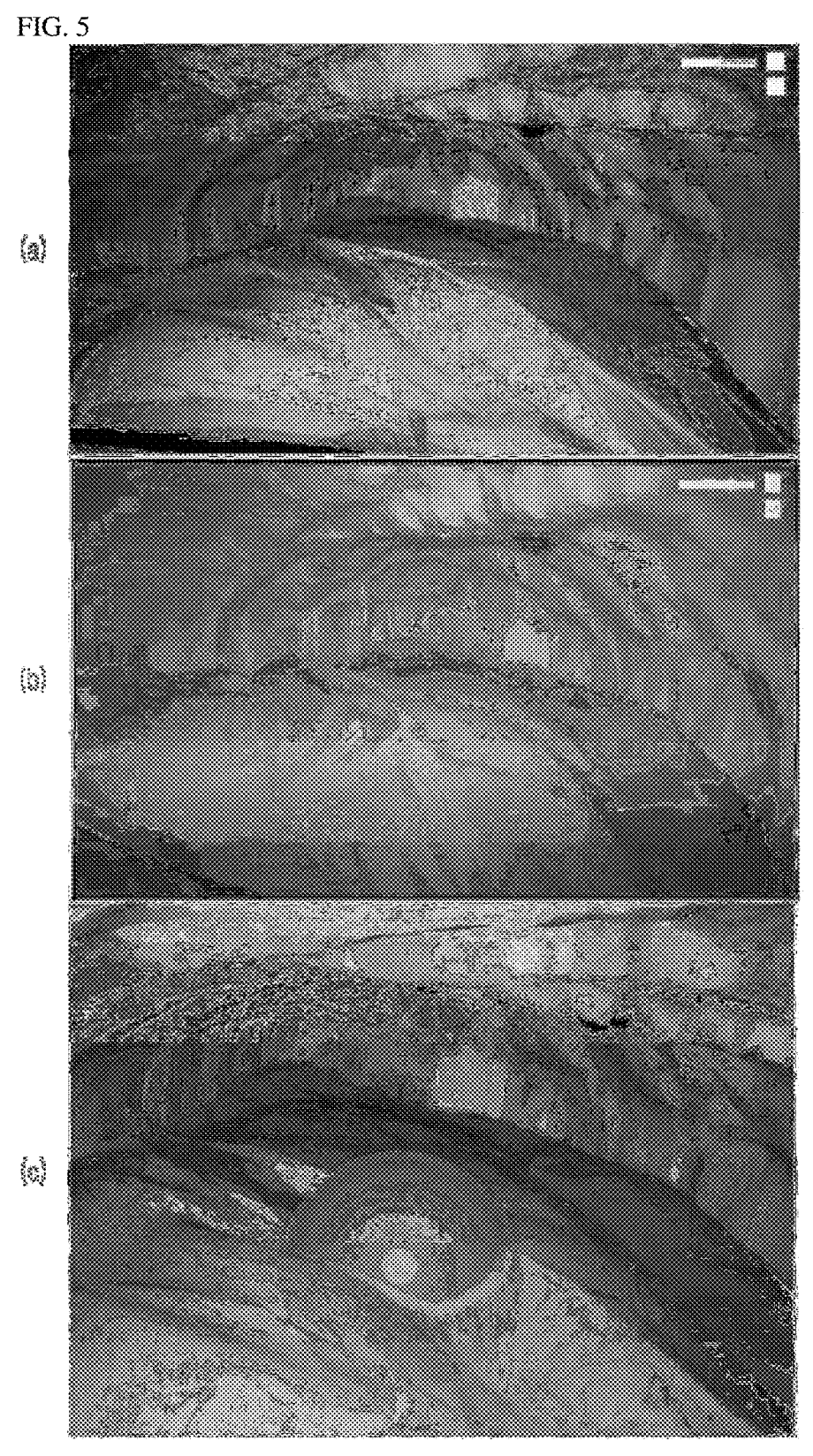
Figures 6, 7:
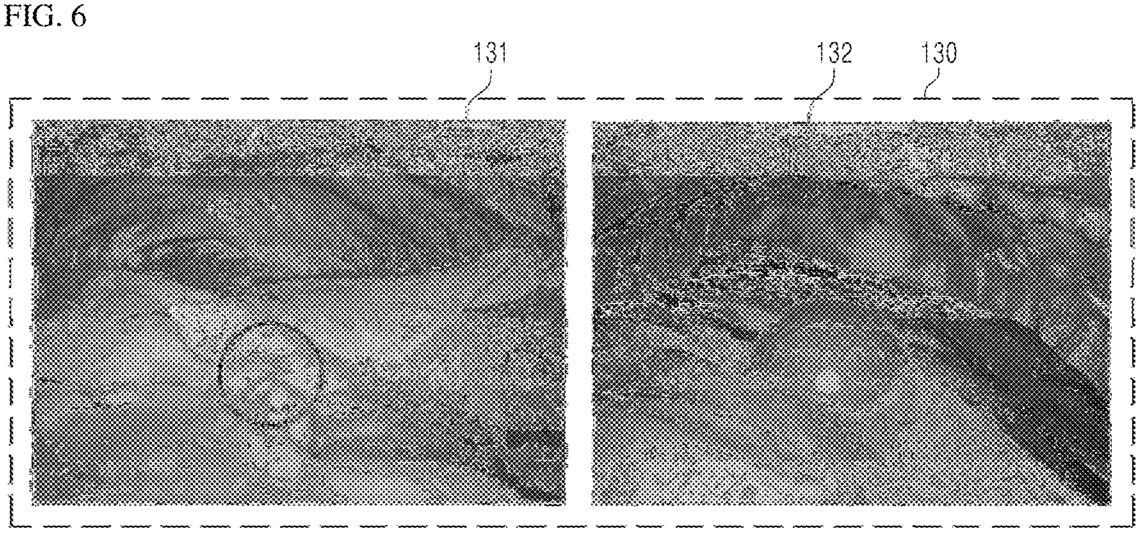
FIG. 6 is an exemplary diagram of simultaneously displaying a thoracoscopic image and a simulation image according to an exemplary embodiment of the present disclosure.
FIG. 7 is a block diagram for schematically explaining the configuration of a thoracoscopy simulation apparatus according to another exemplary embodiment.

FIG. 2 is a block diagram for schematically explaining the configuration of a thoracoscopy simulation apparatus according to an exemplary embodiment of the present disclosure, FIG. 3 is an exemplary diagram illustrating a lung model in a maximal inspiratory state and a lung model in a maximal expiratory state according to an exemplary embodiment of the present disclosure, FIG. 4 is an exemplary diagram for explaining the creation of a 3D atelectasis model in an expiratory state according to an exemplary embodiment of the present disclosure, FIG. 5 is an exemplary diagram illustrating a pulmonary nodule marked on a 3D thorax model and a safe margin for removing the pulmonary nodule according to an exemplary embodiment of the present disclosure, and FIG. 6 is an exemplary diagram of simultaneously displaying a thoracoscopic image and a simulation image according to an exemplary embodiment of the present disclosure. In the following description, redundant parts with the description of FIG. 1 will be omitted.

Referring to FIGS. 2 to 6, the thoracoscopy simulation apparatus 100 may include a thoracoscope 110, a surgical instrument (or surgical tool) 120, a monitor 130, a tracking unit 140, a user interface 150, a storage unit 160, a simulation processing unit 170, and a control unit 180.

The thoracoscope 110 may be inserted into one of holes drilled in a chest to take images of (capture) a surgical site. The images taken by the thoracoscope 110 may be displayed on one (131) of monitors under the control of the control unit 180.

The surgical instrument 120 may be inserted into the remaining holes drilled in the chest, and an operator may manipulate the surgical instrument 120 to perform tissue incision and hemostasis, grasp or peel a mucous membrane, or the like. Here, the surgical instrument 120 may include an incision instrument 121 for incising tissue and performing hemostasis, and a forceps instrument 122 for grasping or peeling the mucous membrane. In this exemplary embodiment, the surgical instrument 120 may further include other instruments in addition to the incision instrument 121 and the forceps instrument 122.

In this exemplary embodiment, the thoracoscope 110 and the surgical instrument 120 may be provided with markers (not illustrated) for tracking their location information. For example, a thoracic marker (not illustrated) may be disposed on one end of the inserted thoracoscope 110, and a surgical instrument marker (not illustrated) may be disposed on one end of the inserted surgical instrument 120. In this exemplary embodiment, the thoracic marker and the surgical instrument marker may have preset reference points stored in the storage unit 160. As will be explained further below, the present disclosure is not limited to using markers, and a gyro sensor, an inertial sensor, an acceleration sensor, etc. may be disposed, instead of the above-described markers, to identify location information about the thoracoscope 110 and the surgical instrument 120 and determine a movement path and a direction of progress based on electrical signals of such sensors and camera images.

The tracking unit 140 may track the thoracic marker, the surgical instrument marker, and markers (not illustrated) attached to a patient. The tracking unit 140 may compare (match, register) the current locations of the thoracic marker and the surgical instrument marker with the reference points stored in the storage unit 160, to identify the location information about the thoracoscope 110 and the surgical instrument 120 with respect to the patient within an image displayed on the monitor 130, and determine the movement path and the direction of progress. In this exemplary embodiment, the tracking unit 140 may identify the location information about the markers using a magnetic field or may identify the location information about the markers by optical marker recognition or optical signal transmission/reception.

In an optional exemplary embodiment, the tracking unit 140 may identify the location information about the thoracoscope 110 and the surgical instrument 120 and determine the movement path and the direction of progress by mounting a gyro sensor, an inertial sensor, an acceleration sensor, etc., instead of the above-described markers, and analyzing electrical signals of those sensors. When using an inertial sensor, the tracking unit 140 may identify the location information, the movement path, posture, and the like related to the thoracoscope 110 and the surgical instrument 120 by object recognition based on feature points of an image of a stereo camera or depth camera, and posture estimation based on measurements of the inertial sensor coupled to the surgical instrument. Lidar cameras, RGBD cameras, etc. may also be used similarly. In this specification, a description is given based on markers, but the scope of the present disclosure is not limited thereto. A person skilled in the art may understand that the present disclosure may be implemented based on the sensors and cameras described above in addition to the markers.

The user interface 150 may include an input interface (not illustrated) and an output interface (not illustrated).

The input interface is a configuration that allows the operator to input information related to the operation and control of the thoracoscopy simulation apparatus 100 and may include, for example, a mouse, a keyboard, etc. In an optional exemplary embodiment, the input interface may further include a microphone (not illustrated) for voice recognition. The microphone which is an example may not be limited in view of its location and implementation method, and input means for inputting audio signals may be used without limitation.

Meanwhile, in this exemplary embodiment, the output interface may include a speaker (not illustrated). The speaker may output information related to the operation of the thoracoscopy simulation apparatus 100 as auditory data. That is, the speaker may output information related to the operation of the thoracoscopy simulation apparatus 100 as audio data. Under the control of the control unit 180, the speaker may output, as audio, notification messages such as warning sounds, notification sounds, and error states, information corresponding to the operator's voice command, processing results in response to the operator's voice command, and the like. The speaker which is an example may not be limited in view of its location and implementation method, and may include any output means for outputting audio signals.

The output interface is a configuration that allows the operator to output information related to the operation and control of the thoracoscopy simulation apparatus 100, namely, a configuration for interfacing with the operator.

That is, the user interface 150 may be configured so that the operator may check information related to the thoracoscopy simulation apparatus 100 as well as inputting information related to the thoracoscopy simulation apparatus 100, and may include a control panel that enables input and output. Here, the control panel may include the monitor 130 described above. The user interface 150 may include, for example, a certain display member that is sensitive to touches.

Reference points for thoracoscopy simulation may be stored in the storage unit 160. In one exemplary embodiment, reference points in the world coordinate system for tracking the locations of the thoracoscope 110 and the surgical instrument 120 may be stored. The tracking unit 140 may perform calibration for matching a coordinate system of the thoracoscope 110 (which may be based on a coordinate system of the marker attached to the thoracoscope 110) and a coordinate system of the patient (which may be based on a coordinate system of a marker attached to the patient) with the world coordinate system. When using a marker in the matched coordinate system, the tracking unit 140 may determine the location of the thoracoscope with respect to the patient by tracking the location of the marker attached to the thoracoscope, simulate a 3D atelectasis model based on the location, and display a portion corresponding to a field of view (FOV) of the thoracoscope 110 on one (132) of the monitors. The tracking unit 140 may estimate the postures of the thoracoscope 110 and the surgical instrument 120 based on the inertial sensors of the thoracoscope 110 and the surgical instrument 120.

The storage unit 160 may store patient information, such as the patient's surgical posture and the patient's chest CT image. In one exemplary embodiment, the patient's surgical posture may be designated by the operator's decision or may be changed by tracking the location of the marker attached to the patient. Additionally, the patient's chest CT image may include a plurality of slice images taken while the patient is in a maximal inspiratory state, and some of the plurality of slice images may include a pulmonary nodule.

The storage unit 160 may further store the patient's body information, for example, location information about ribs, to create a 3D thorax model. Here, the location information about the ribs may be calculated from the patient's chest CT image and stored.

The simulation processing unit 170 may generate a 3D lung model, a 3D atelectasis model, and a 3D thorax model using the patient's surgical posture decided based on the marker attached to the patient or the operator's FOV and the patient's chest CT image. The simulation processing unit 170 may generate a simulation image of the 3D atelectasis model based on the tracked location of the thoracoscope 110 or location of the surgical instrument 120 and the 3D thorax model. The simulation image generated by the simulation processing unit 170 may be output to one (132) of the monitors under the control of the control unit 180.

The simulation processing unit 170 may generate a 3D lung model with a pulmonary nodule marked, based on a chest CT image of the patient in an inspiratory state. In this exemplary embodiment, the simulation processing unit 170 may generate a 3D lung model based on the chest CT image of the patient in the inspiratory state stored in the storage unit 160. In one exemplary embodiment, the simulation processing unit 170 may mark (display) the location of the pulmonary nodule on the generated 3D lung model. In order to create the 3D lung model, the simulation processing unit 170 may segment a lung part based on intensity values of pixels or voxels from the chest CT image of the patient in the inspiratory state. The explanation below takes pixels as an example, but in the case of a 3D segmentation algorithm, etc., the segmentation may also be performed on a voxel basis.

Basically, in a chest CT image, a lung part is in the darkest color in a body because the lungs are filled with air, and muscles, bones, and other organs appear generally white, so the lungs and other organs may be distinguished from each other by recognizing a difference in intensity of pixels in the image. For a digitized chest CT image, windows each having a certain pixel size may be set, a contrast difference within each window may be calculated while moving from an upper left to a lower right, and a location where the calculated value is large may be memorized. Each memorized location may be connected with a line to mark off one low-intensity area, and in this way, the lungs and other organs may be distinguished from each other in the chest CT image. Such a boundary may mean a contour in a 3D volume. By extracting the contours indicating the lung part from a plurality of chest CT images taken in three directions, the resolution of each chest CT image, that is, distances between the taken time points for acquiring the respective images may be calculated and the contours may be arranged in proportion to the distances.

The contour generated based on the memorized location may have spatial vertices that define the contour, and the number of vertices may vary depending on the computing capacity of a processing device or the resolution of the monitor 130 for real-time simulation of the 3D atelectasis model. Therefore, in order to effectively create a 3D lung model, the number of vertices defining each contour may be matched and the lines may be simplified. The simulation processing unit 170 of the apparatus performing this task may set the sequence of points in space. The simulation processing unit 170 may align starting points of this sequence as closely as possible. Afterwards, the simulation processing unit 170 may generate lines perpendicular to a direction of the chest CT image by connecting vertices of specified sequences of each contour, for example, the $10^{th}$, $20^{th}$, and $30^{th}$ vertices of a contour a and the $10^{th}$, $20^{th}$, and $30^{th}$ vertices of a contour b right below the contour a. Through this, a 3D model may be created based on the thusly-obtained lines and the contours extracted from the chest CT images. Since an outer surface defined through the above step is a virtual surface created by the lines, it is necessary to convert the outer surface into a mesh-type figure to define it accurately. A mesh, which is the smallest unit of surface in computer graphics, is a surface defined within three lines connecting three points. Therefore, a 3D lung model may be defined by a plurality of (e.g., hundreds of thousands of) vertices.

The simulation processing unit 170 may change (modify) a 3D lung model in an inspiratory state to create a 3D atelectasis (collapsed lung) model in an expiratory state. Referring to FIG. 3, (a) of FIG. 3 illustrates a 3D lung model in a maximal inspiratory state, and (b) of FIG. 3 illustrates a 3D atelectasis model in a maximal expiratory state. Chest CT scanning for finding pulmonary nodules is performed, as illustrated in (a) of FIG. 3, when a patient is in a maximal inspiratory state, and the result of the CT scanning is an image taken when the lungs are at their largest size. However, during the actual surgery to remove a pulmonary nodule, it is performed in the patient's expiratory state and the lungs become an atelectasis state that the lungs are collapsed due to gravity depending on the patient's posture, that is, a state as illustrated in (b) of FIG. 3. Therefore, there may be a big gap between the location of the pulmonary nodule seen in the chest CT image and the lung condition and location of the pulmonary nodule seen in the actual surgery. Accordingly, in this exemplary embodiment, the simulation processing unit 170 may eliminate the above-described gap by changing (modifying) the previously generated 3D lung model and generating a 3D atelectasis model in an expiratory state.

The simulation processing unit 170 may determine the direction of gravity based on the location of a marker or the patient's posture decided by the FOV of a medical staff (e.g., the operator). Here, the patient's posture may include the surgical posture of the patient, who is scheduled to get surgery, depending on the location of a pulmonary nodule. The simulation processing unit 170 may generate a 3D atelectasis model by shifting the locations of at least some vertices included in a 3D lung model based on the determined direction of gravity. In this exemplary embodiment, the simulation processing unit 170 may rotate the 3D lung model to match the patient's posture. Thereafter, the simulation processing unit 170 may generate a 3D atelectasis model through a process of reducing a gap between the respective vertices and simultaneously shifting each vertex by a certain distance in the direction of gravity according to the surgical posture in the 3D lung model in the inspiratory state.

FIG. 4 conceptually illustrates the process of generating a 3D atelectasis model. When explaining a 3D atelectasis model generation of the simulation processing unit 170 with reference to FIG. 4, the simulation processing unit 170 may generate the 3D atelectasis model by loading a plurality of vertices included in a 3D lung model and moving the locations of all or some of vertices segmented for simulation. Referring to (a) of FIG. 4, for the sake of explanation, some of the vertices illustrated in (a) of FIG. 4 are indicated as a first vertex 411, a second vertex 412, and a third vertex 413.

The simulation processing unit 170 may load a plurality of vertices included in a 3D lung model (or a 3D lung model in an inspiratory state) and then generate a virtual ground for movement limit of the vertices based on the direction of gravity. Referring to (b) of FIG. 4, a regenerated figure is located on a virtual ground 420.

The simulation processing unit 170 may calculate distances from the ground to the vertices constituting the figure using a simulation resolution. From (c) of FIG. 4, the simulation processing unit 170 may calculate a first distance d1 from the ground 420 to the first vertex 411, a second distance d2 from the ground 420 to the second vertex 412, and a third distance d3 from the ground 420 to the third vertex 413.

The simulation processing unit 170 may move (shift) the locations of at least some vertices in the direction of gravity based on the distances. Here, moving the locations of at least some vertices in the direction of gravity based on the distances may include moving vertices farther from the ground by longer distances toward the ground. This may include the meaning of moving vertices more affected by gravity toward the ground by longer distances because vertices farther from the ground are more affected by gravity.

From (c) of FIG. 4, if it is assumed that the second distance d2 is the longest among the first distance d1, the second distance d2, and the third distance d3, and the first distance d1 and the third distance d3 are the same, the simulation processing unit 170 may move the second vertex 412 by a longer distance toward the ground than the first and third vertices 411 and 413.

In an optional exemplary embodiment, the simulation processing unit 170 may move each vertex by a distance of the same preset ratio. From (c) of FIG. 4, the simulation processing unit 170 may move the vertices by setting a ratio for moving the second vertex 412 toward the ground with respect to the second distance d2 to be the same as a ratio for moving the first and third vertices 411 and 413 toward the ground with respect to the first and third distances d1 and d3.

In an optional exemplary embodiment, the simulation processing unit 170 may move at least two vertices among vertices to be moved by distances of different ratios. Here, it may be included that a rate for moving the corresponding vertex toward the ground has been preset for each distance. Here, the different ratios may be stored in the storage unit 160 in advance through experimentation so as to be applied for each distance. From (c) of FIG. 4, a first ratio for moving the second vertex 412 toward the ground with respect to the second distance d2 may be preset, so the simulation processing unit 170 may move the second vertex 412 at the first ratio. In addition, a second ratio for moving the first and third vertices 411 and 413 toward the ground with respect to the first and third distances d1 and d3 may be preset, so the simulation processing unit 170 may move the first and third vertices 411 and 413 at the second ratio. Here, it can be seen that the first ratio and the second ratio are different from each other and the first ratio (e.g., 70% compared to 100%) is larger than the second ratio (e.g., 30% compared to 100%).

In an optional exemplary embodiment, the simulation processing unit 170 may generate sub-vertices that the distance is divided into a preset number of equal parts and adjust a rate for moving each sub-vertex toward the ground. As illustrated in (d) of FIG. 4, for example, first to sixth sub-vertices 431 to 436 may be generated by dividing the first distance d1 into a preset number of equal parts. Here, the first sub-vertex 431 may be the same as the above-described first vertex 411 and the sixth sub-vertex 436 may be in contact with the ground 420. Here, a method of adjusting the rates for moving the first to sixth sub-vertices 431 to 436 toward the ground is the same as that illustrated in (c) of FIG. 4, so a description thereof will be omitted.

Although the exemplary embodiments described above are conceptually simply explained as if each vertex moves vertically toward the ground, it may be calculated such that each vertex is moved while being affected by other adjacent vertices. For example, vertices located at both protruding points of a folded structure may have shorter movement lengths toward the ground than vertices located at protruding points of an unfolded structure, and may move in a diagonal direction with respect to the ground.

Additionally, 3D vertices (hereinafter, referred to as organ vertices) of stomach, thorax, etc. may be configured to form a separate group from the vertices discussed above. The organ vertices may have a function of calculating in real time distances from the lung vertices, which are moving in the direction of gravity, and when coming within a specified distance, switching the movement direction of the lung vertices into adjacent organ vertices located at lower positions. Accordingly, the lung vertices have an effect of moving in the direction of gravity according to the shape of the surface of thorax vertices, which is the inner shape of a ball, to gather at the bottom of the thorax, and moving along the outer surface of the stomach vertex having the outer shape of a ball. The above method is an atelectasis (collapsed lung) simulation that reflects the surface shape of internal organs in an actual atelectasis state.

The simulation processing unit 170 may generate a 3D atelectasis model based on vertices whose locations have been moved under the effect of gravity and perform surface rendering. In order to easily analyze 3D data, a graphical visualization technique is essential, and surface rendering may be performed for this purpose. Surface rendering is a visualization method that expresses the locations of specific scalar values for vertices as a basic figure and it can be said to be a three-dimensional extension of a two-dimensional contour. Hereinafter, the content related to surface rendering is known and a detailed description thereof will be omitted.

Once the 3D atelectasis model is generated as described above, the simulation processing unit 170 may generate a 3D thorax model using the 3D atelectasis model and the locations of ribs included in the chest CT image. (a) of FIG. 5 illustrates a 3D thorax model generated using the 3D atelectasis model and the patient's rib location information. The 3D thorax model, including the 3D atelectasis model, may be displayed on one (132) of the monitors.

Once the 3D thorax model is generated, the simulation processing unit 170 may mark the location of a pulmonary nodule on the 3D atelectasis model. (b) of FIG. 5 illustrates an example where the location (pink) of a pulmonary nodule is marked on the 3D atelectasis model included in the 3D thorax model. As for the location of the pulmonary nodule in the 3D atelectasis model, in one exemplary embodiment, the location of a pulmonary nodule may be set in a 3D lung model and moved along with the movement of the vertices by gravity.

Based on the location of the pulmonary nodule, the simulation processing unit 170 may indicate (mark) a safe margin (green ball in (c) of FIG. 5), which indicates a removal range around the pulmonary nodule, to distinguish the pulmonary nodule from the surrounding tissues. Here, the simulation processing unit 170 may display on the monitor 130 an interface (not illustrated, which may be a visible or audible interface) for changing the size or mark of the safe margin, and change the size or mark of the safe margin based on the medical staff's input through the interface.

The simulation processing unit 170 may position the 3D thorax model in a virtual space and generate a simulation image based on the 3D thorax model and the tracked location of the thoracoscope 110 or the surgical instrument 120. Here, the simulation image may include an image obtained by applying the location-tracked result of the thoracoscope 110 or the location-tracked result of the surgical instrument 120 using a marker or sensor to the 3D thorax model.

In an optional exemplary embodiment, the simulation processing unit 170, as illustrated in (a) to (c) of FIG. 5, may load the 3D thorax model or display the 3D thorax model on the monitor 130, then receive the degree of change of the 3D atelectasis model through the user interface 150, and additionally change the 3D atelectasis model based on the degree of change. This is to reduce a gap caused by a difference between an actual surgery image and the simulation image, and may be performed by manipulation by the operator or surgical assistant.

In an optional exemplary embodiment, when the simulation image is generated, the simulation processing unit 170 may simultaneously display the thoracoscopic image taken by the thoracoscope 110, the simulation image, and a part of the 3D atelectasis model corresponding to the FOV of the thoracoscope 100 based on the location of the thoracoscope 110. FIG. 6 illustrates an example of simultaneously displaying the thoracic image and the simulation image on the monitor 130.

In one exemplary embodiment, the simulation processing unit 170 may compare a ratio of the lung part to the thorax in the thoracoscopic image and the simulation image simultaneously displayed on the monitor 130, and when the difference value exceeds a reference value, the simulation processing unit 170 may additionally change the 3D atelectasis model based on the ratio of the lung part in the thoracoscopic image. For example, the simulation processing unit 170 may additionally change the 3D atelectasis model based on a comparison result of a distance from a thorax (chest) to an actual collapsed lung (atelectasis) in the left 3D thoracoscopy image in FIG. 6 with a distance from the thorax to the simulated collapsed lung in the right simulation image.

In an optional exemplary embodiment, the simulation processing unit 170 may transmit the simulation image to a wearable device (not illustrated) worn by the operator through a network (not illustrated).

The control unit 180 is a type of central processing device and may control the whole operation of the thoracoscopy simulation apparatus 100. The control unit 180 or simulation processing unit 170 may include all types of devices that can process data, such as a processor. Here, 'processor' may mean, for example, a data processing device built into hardware that has a physically structured circuit to perform functions expressed by codes or instructions included in a program. An example of the data processing device built into hardware may include a microprocessor, a central processing unit (CPU), a processor core, a multiprocessor, an application-specific integrated circuit (ASIC), a field programmable gate array (FPGA), or the like, but the scope of the present disclosure is limited thereto.

FIG. 7 is a block diagram for schematically explaining the configuration of a thoracoscopy simulation apparatus according to another exemplary embodiment. In the following description, redundant parts with the description of FIGS. 1 to 6 will be omitted.

In this exemplary embodiment, a processor 191 may process the functions performed by the tracking unit 140, the user interface 150, the storage unit 160, the simulation processing unit 170, and the control unit 180 illustrated in FIG. 2.

The processor 191 may control the entire operation of the thoracoscopy simulation apparatus 100. Here, 'processor' may mean, for example, a data processing device built into hardware that has a physically structured circuit to perform functions expressed by codes or instructions included in a program. An example of the data processing device built into hardware may include a microprocessor, a central processing unit (CPU), a processor core, a multiprocessor, an application-specific integrated circuit (ASIC), a field programmable gate array (FPGA), or the like, but the scope of the present disclosure is limited thereto.

A memory 192 may be operably connected to the processor 191 and store at least one code in association with an operation performed by the processor 191.

Additionally, the memory 192 may perform the function of temporarily or permanently storing data processed by the processor 191. Here, the memory 192 may include magnetic storage media or flash storage media, but the scope of the present disclosure is not limited thereto. Such memory 192 may include an internal memory and/or an external memory, and may include a volatile memory such as DRAM, SRAM, or SDRAM, a non-volatile memory such as one time programmable ROM (OTPROM), PROM, EPROM, EEPROM, mask ROM, flash ROM, NAND flash memory, or NOR flash memory, a flash drive such as SSD, compact flash (CF) card, SD card, micro-SD card, mini-SD card, Xd card, or memory stick, or a storage device such as HDD.

Figure 8:
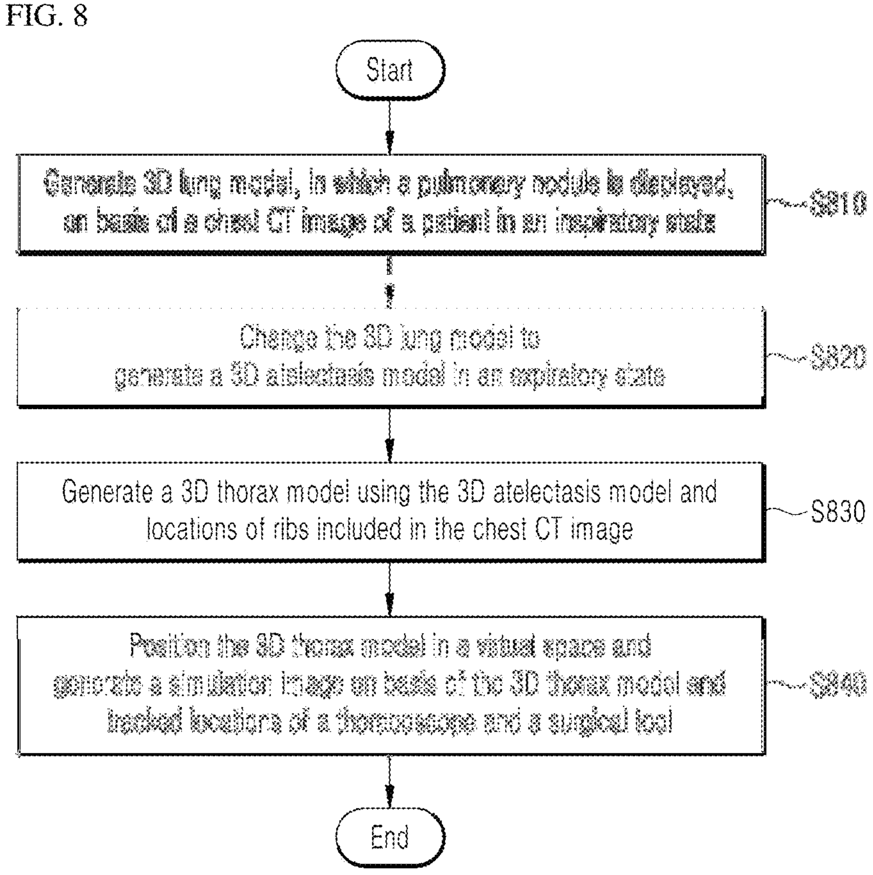
FIG. 8 is a flowchart for explaining a thoracoscopy simulation method according to an exemplary embodiment of the present disclosure.

FIG. 8 is a flowchart for explaining a thoracoscopy simulation method according to an exemplary embodiment of the present disclosure. The thoracoscopy simulation method according to this exemplary embodiment may be performed by the processor 191 provided in the thoracoscopy simulation apparatus 100. In the following description, redundant parts with the description of FIGS. 1 to 7 will be omitted.

Referring to FIG. 8, in step S810, the processor 191 may generate a 3D lung model, in which a pulmonary nodule is marked, based on a chest CT image of a patient in an inspiratory state.

In step S820, the processor 191 may change the 3D lung model to generate a 3D atelectasis model in an expiratory state. When generating the 3D atelectasis model, the processor 191 may generate the 3D atelectasis model by determining the direction of gravity based on the patient's surgical posture, and moving the locations of at least some vertices included in the 3D lung model based on the direction of gravity. Specifically, the processor 191 may load a plurality of vertices or models included in the 3D lung model to generate the 3D atelectasis model. The processor 191 may generate a ground for the movement limit of the vertices based on the direction of gravity. The processor 191 may calculate distances from the ground to the vertices. The processor 191 may move the locations of at least some vertices in the direction of gravity based on the distances. Here, moving the locations of at least some vertices in the direction of gravity based on the distances may include moving a vertex farther from the ground by a longer distance toward the ground. In addition, moving the vertex farther from the ground by a longer distance toward the ground may include moving the distance for each vertex at the same preset ratio, or moving the distances of at least two of the vertices to be moved at different ratios. The processor 191 may generate the 3D atelectasis model including vertices which have changed in locations. In addition, the processor 191 may calculate in real time distances between the vertices and vertices of a stomach and thorax generated based on CT. As moving in the direction of gravity, when the distances are shortened, the processor 191 may change the next moving direction toward adjacent vertices located below.

In step S830, the processor 191 may generate a 3D thorax model using the 3D atelectasis model and the locations of ribs included in the chest CT image. In one exemplary embodiment, the processor 191 may mark (display) the location of a pulmonary nodule on the 3D atelectasis model, and display a safe margin, which indicates a removal range, around the pulmonary nodule based on the location of the pulmonary nodule, to be distinguished from surrounding tissues. Additionally, the processor 191 may display an interface for changing the size or mark of the safe margin and change the size or mark of the safe margin based on an input through the interface. In an optional exemplary embodiment, the processor 191 may render the 3D thorax model to display the 3D thorax model on the monitor 130, receive the degree of change of the 3D atelectasis model through the user interface 150, and additionally change the 3D atelectasis model based on the degree of change. This is to reduce a gap caused by a difference between an actual surgery image and a simulation image, and may be performed by manipulation by the operator or surgical assistant.

In step S840, the processor 191 may position the 3D thorax model in a virtual space and generate a simulation image based on the 3D thorax model and the tracked locations of the thoracoscope and the surgical instrument. Here, the simulation image may include an image obtained by applying the location-tracked result of the thoracoscope 110 or the location-tracked result of the surgical instrument 120 using a marker or sensor to the 3D thorax model.

In an optional exemplary embodiment, when a simulation image is generated, the processor 191 may simultaneously display a thoracoscopic image taken by the thoracoscope 110 and the simulation image on different screens. The simulation image may simulate a portion of the 3D atelectasis model corresponding to the FOV at the location of the thoracoscope. In an optional exemplary embodiment, the processor 191 may compare a ratio of a lung part to the thorax in the thoracoscopic image and the simulation image simultaneously displayed on the monitor 130, and when a difference value exceeds a reference value, the processor 191 may additionally change the 3D atelectasis model based on the ratio of the lung part in the thoracoscopic image. In an optional exemplary embodiment, the processor 191 may transmit the simulation image to a wearable device (not illustrated) worn by the operator through a network (not illustrated).

Embodiments according to the present disclosure described above may be implemented in the form of computer programs that may be executed through various components on a computer, and such computer programs may be recorded in a computer-readable medium. Examples of the computer-readable medium may include, but are not limited to: magnetic media such as hard disks, floppy disks, and magnetic tapes; optical media such as CD-ROM disks and DVD-ROM disks; magneto-optical media such as floptical disks; and hardware devices that are specially configured to store and execute program commands, such as ROM, RAM, and flash memory devices.

Meanwhile, the computer programs may be those specially designed and constructed for the purposes of the present disclosure or they may be of the kind well known and available to those skilled in the computer software arts. Examples of program code include both machine codes, such as produced by a compiler, and higher level code that may be executed by the computer using an interpreter.

As used in the present disclosure (especially in the appended claims), the singular forms "a," "an," and "the" include both singular and plural references, unless the context clearly states otherwise. Also, it should be understood that any numerical range recited herein is intended to include all sub-ranges subsumed therein (unless expressly indicated otherwise) and accordingly, the disclosed numeral ranges include every individual value between the minimum and maximum values of the numeral ranges.

Operations constituting the method of the present disclosure may be performed in appropriate order unless explicitly described in terms of order or described to the contrary. The present disclosure is not necessarily limited to the order of operations given in the description. All examples described herein or the terms indicative thereof ("for example," etc.) used herein are merely to describe the present disclosure in greater detail. Therefore, it should be understood that the scope of the present disclosure is not limited to the exemplary embodiments described above or by the use of such terms unless limited by the appended claims. Also, it should be apparent to those skilled in the art that various modifications, combinations, and alternations can be made depending on design conditions and factors within the scope of the appended claims or equivalents thereof.

Therefore, technical ideas of the present disclosure are not limited to the above-mentioned embodiments, and it is intended that not only the appended claims, but also all changes equivalent to claims, should be considered to fall within the scope of the present disclosure.

The invention claimed is:

1. A thoracoscopy simulation method in which each step is performed by a processor, the thoracoscopy simulation method comprising steps of:

generating a three-dimensional (3D) lung model, in which a pulmonary nodule is displayed, the 3D lung model being generated based on a chest CT image of a patient in an inspiratory state;

generating a 3D atelectasis model in an expiratory state by changing the 3D lung model;

generating a 3D thorax model by using the 3D atelectasis model and locations of ribs included in the chest CT image; and positioning the 3D thorax model in a virtual space and generating a simulation image based on the 3D thorax model and tracked locations of a thoracoscope and a surgical instrument, wherein the step of generating the 3D atelectasis model includes:

determining a direction of gravity based on a posture of the patient;

loading a plurality of vertices included in the 3D lung model;

generating a virtual ground based on the direction of gravity for movement limit of the vertices;

calculating distances from the ground to the vertices respectively;

moving locations of at least some vertices respectively in the direction of gravity by a movement distance that is determined based on a calculated distance from the ground to each vertex and a preset ratio, and generating the 3D atelectasis model including the vertices whose locations have been moved and performing surface rendering, and wherein the step of moving locations of at least some vertices respectively includes moving a vertex farther from the ground by a longer distance toward the ground.

2. The thoracoscopy simulation method of claim 1, wherein the step of generating the 3D thorax model includes generating the 3D thorax model based on the locations of the ribs included in the chest CT image.

3. The thoracoscopy simulation method of claim 1, further comprising:

forming organ vertices including stomach and thorax in addition to the plurality of vertices included in the 3D lung model;

calculating in real time distances between moving vertices of the lung model and the organ vertices based on the direction of gravity; and when the distances are within a preset certain distance, switching a moving direction of the vertices of the lung model to the organ vertices around a lung located at a relatively low position.

4. The thoracoscopy simulation method of claim 1, wherein the step of generating the 3D thorax model further includes:

displaying a location of the pulmonary nodule on the 3D atelectasis model; and displaying a safe margin, which indicates a removal range, around the pulmonary nodule based on the location of the pulmonary nodule, to be distinguished from surrounding tissues.

5. The thoracoscopy simulation method of claim 4, further comprising:

displaying an interface for changing a size or display of the safe margin; and changing the size or display of the safe margin based on an input through the interface.

6. The thoracoscopy simulation method of claim 1, further comprising:

receiving an input of a degree of change of the 3D atelectasis model; and additionally changing the 3D atelectasis model based on the degree of change.

7. The thoracoscopy simulation method of claim 1, further comprising, after generating the simulation image, simultaneously displaying a thoracoscopic image taken by the thoracoscope and the simulation image on different screens.

8. The thoracoscopy simulation method of claim 7, further comprising:

comparing ratios of lung parts in the thoracoscopic image and the simulation image; and additionally changing the 3D atelectasis model based on the ratios of the lung parts.

9. The thoracoscopy simulation method of claim 1, further comprising, after generating the simulation image, transmitting the simulation image to a wearable device worn by an operator.

10. A thoracoscopy simulation apparatus comprising:

a processor; and a memory that is operably connected to the processor and stores at least one code to be performed by the processor, wherein when the memory is executed through the processor, the memory stores a code that causes the processor to generate a three-dimensional (3D) lung model, in which a pulmonary nodule is displayed, based on a chest CT image of a patient in an inspiratory state, generate a 3D atelectasis model in an expiratory state by changing the 3D lung model, generate a 3D thorax model by using the 3D atelectasis model and locations of ribs included in the chest CT image, and position the 3D thorax model in a virtual space and generate a simulation image based on the 3D thorax model and tracked locations of a thoracoscope and a surgical instrument, wherein the memory, when generating the 3D atelectasis model, stores a code that causes the processor to determine a direction of gravity based on a posture of the patient, load a plurality of vertices included in the 3D lung model, generate a virtual ground based on the direction of gravity for movement limit of the vertices, calculate distances from the ground to the vertices respectively, move locations of at least some vertices respectively in the direction of gravity by a movement distance that is determined based on a calculated distance from the ground to each vertex and a preset ratio, and generate the 3D atelectasis model including the vertices whose locations have been moved and perform surface rendering, and wherein the memory, when moving the locations of at least some vertices respectively, stores a code that causes the processor to move a vertex farther from the ground by a longer distance toward the ground.

11. The thoracoscopy simulation apparatus of claim 10, wherein the memory stores a code that causes the processor to move at least two of the vertices by using a plurality of preset ratios when moving the vertex farther from the ground by the longer distance toward the ground.

12. The thoracoscopy simulation apparatus of claim 10, wherein the memory further stores a code that causes the processor to display a location of the pulmonary nodule on the 3D atelectasis model, and display a safe margin, which indicates a removal range, around the pulmonary nodule based on the location of the pulmonary nodule, to be distinguished from surrounding tissues, when generating the 3D thorax model.

* * * * *